United States Patent [19]

Toye

[11] 4,364,391

[45] Dec. 21, 1982

[54] TRACHEOSTOMY APPARATUS AND METHOD

[76] Inventor: Frederic J. Toye, 275 Old Ranch Rd., Seal Beach, Calif. 90730

[21] Appl. No.: 206,709

[22] Filed: Nov. 14, 1980

[51] Int. Cl.³ ............................................. A61F 17/32
[52] U.S. Cl. .............................. 128/305.3; 128/214.4; 128/207.15
[58] Field of Search ...................... 128/305.3, 349, 351, 128/207.19, 207.15, 207.16, 200.26, 214.4

[56] References Cited

U.S. PATENT DOCUMENTS

| | | | |
|---|---|---|---|
| 3,511,243 | 5/1970 | Toy | 128/305.3 |
| 3,742,958 | 7/1973 | Rundles | 128/349 R X |
| 3,854,484 | 12/1974 | Jackson | 128/207.15 |
| 4,239,042 | 12/1980 | Asai | 128/214.4 |

*Primary Examiner*—Stephen C. Pellegrino
*Attorney, Agent, or Firm*—Fulwider, Patton, Rieber, Lee & Utecht

[57] ABSTRACT

An apparatus and method for performing percutaneous or non-dissection tracheostomies. An outer needle coaxially slidably receives an inner needle which is attached to a syringe adapted for use in inserting the needles within the tracheal lumen. Operation of the syringe confirms proper location of the needles within the lumen. An elongated dilator coaxially slidably mounts a trachea tube, and its proximal extremity constitutes an introducer portion which tapers to a distal end to which is attached an elongated, flexible leader adapted for insertion through a bore of the outer needle subsequent withdrawal of the inner syringe needle. A slot in the outer needle enables lateral separation of the leader from the outer needle to allow removal of the outer needle from the trachea. The dilator includes a recessed cutting edge for cutting tissue compressed against it during forcible insertion of the introducer portion into the tracheal lumen along the path defined by the leader. The dilator is slidably removable to leave the tracheal tube in breathing position.

11 Claims, 16 Drawing Figures

U.S. Patent  Dec. 21, 1982  Sheet 1 of 3  4,364,391
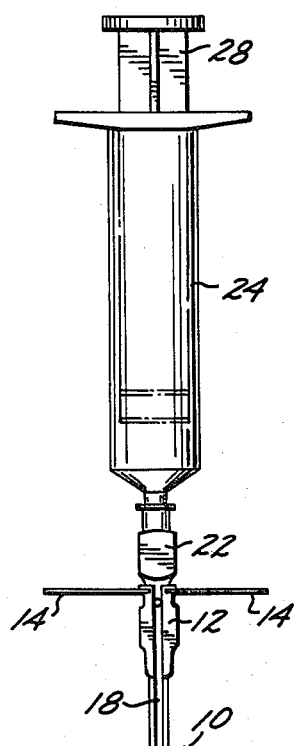
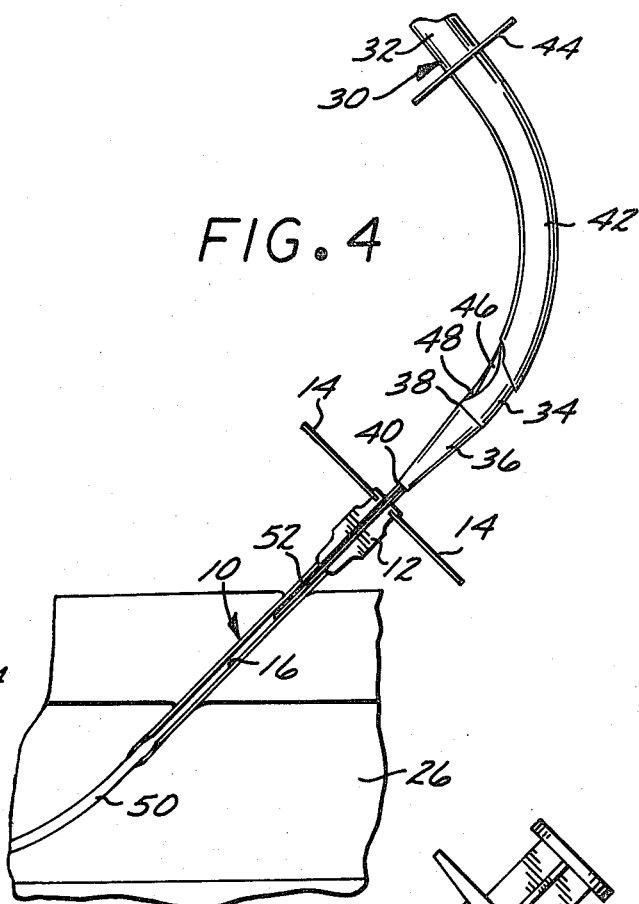
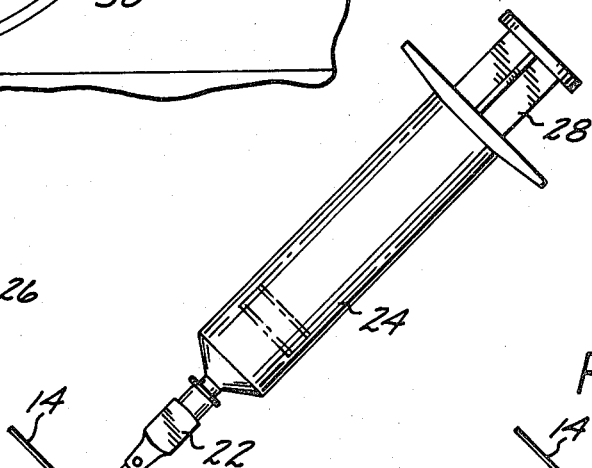
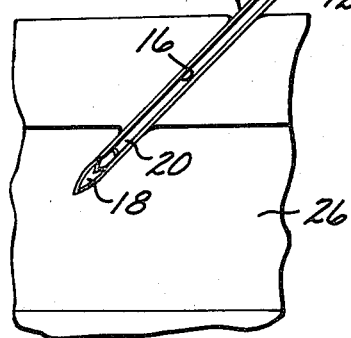

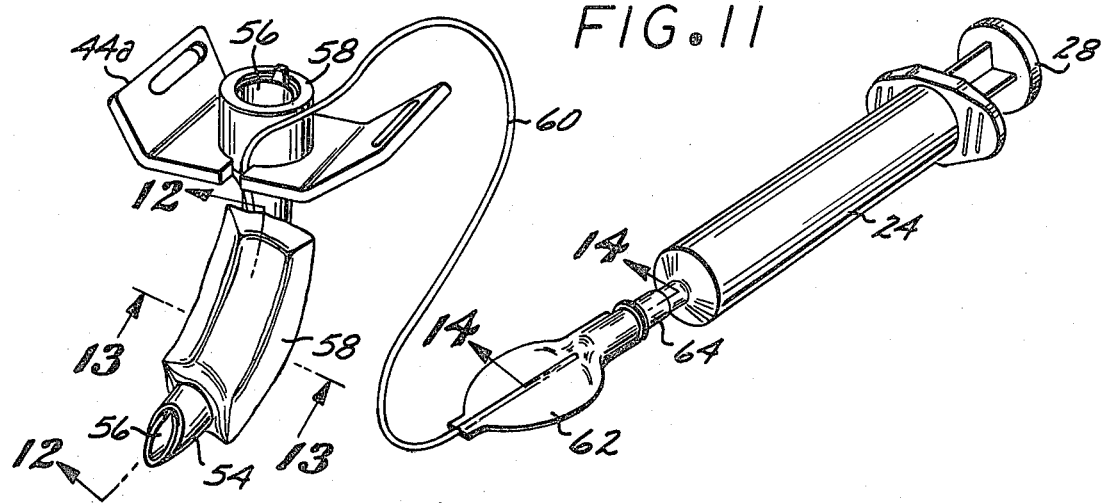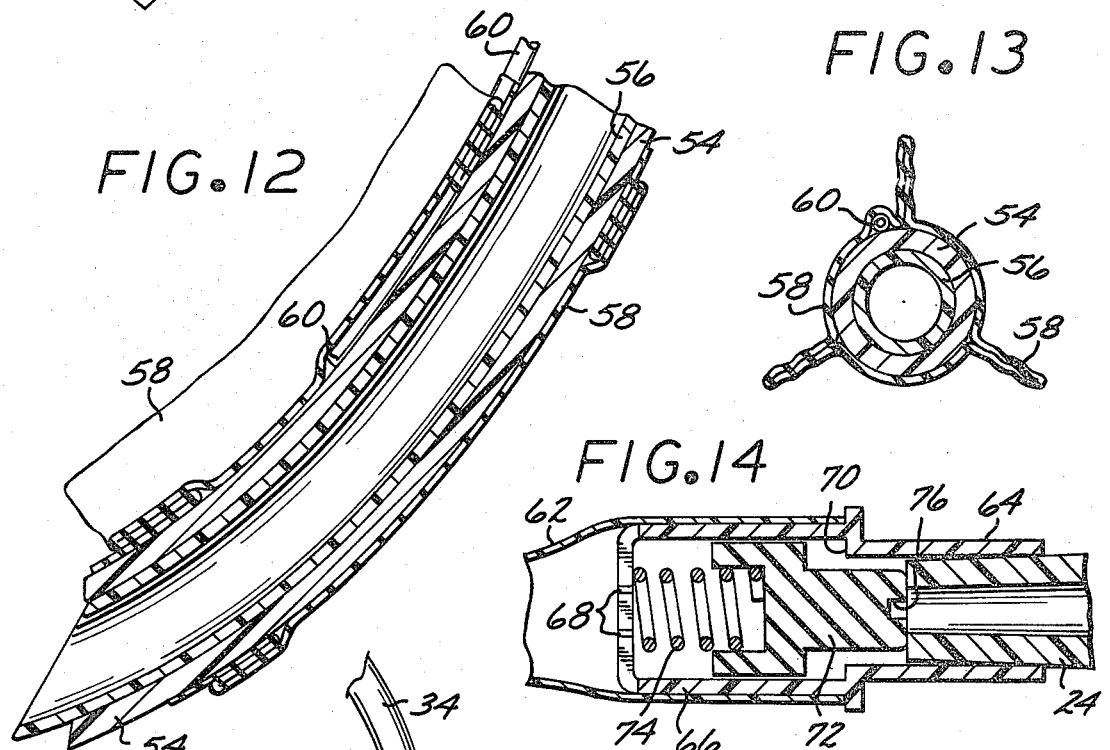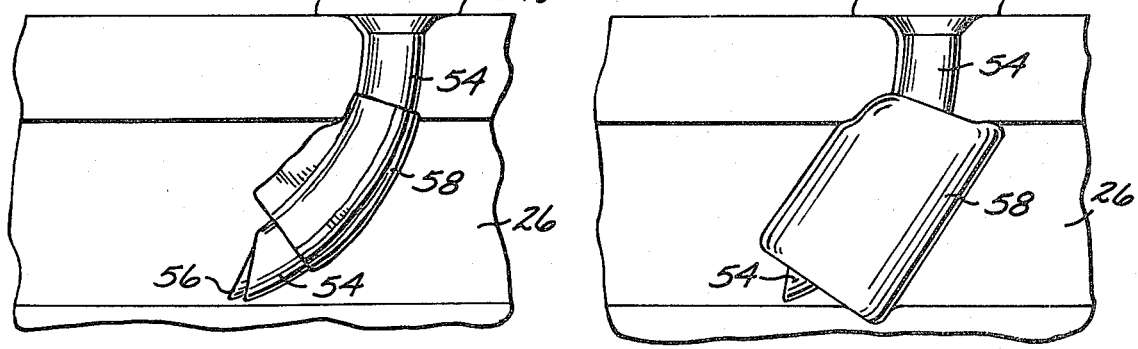

TRACHEOSTOMY APPARATUS AND METHOD

BACKGROUND OF THE INVENTION

1. Field of the Invention

The present invention relates to a tracheostomy apparatus and method to enable breathing when the upper portion of the throat is obstructed.

2. Description of the Prior Art

A number of devices have been advanced for performing non-dissection tracheostomies. Such devices are normally preferable to dissection tracheostomy procedures, which require considerable surgical skill in that the neck area is highly vascular, including many blood vessels which tend to bleed profusely during a dissection procedure.

U.S. Pat. No. 2,991,787, issued July 11, 1961 for "Tracheotomy Instrument" is typical of such devices. The device of that patent is essentially a cutting instrument, being characterized at its distal end by a plurality of blades which cut through the body tissues as the device is forced into the tracheal lumen. Consequently, its use if often accompanied by profuse bleeding. In addition, the device includes a leader which passes into the tracheal lumen in advance of the remainder of the device. This leader is sufficiently inflexible that, although it has a rounded end, it is susceptible to penetration of the tracheal wall and associated tissues such as the esophagus or large neck vessels.

My U.S. Pat. No. 3,511,243, issued May 12, 1970 for "Apparatus for Providing a Breathing Conduit Communicating with the Trachea at the Base of the Neck," discloses apparatus which meets some of the just-mentioned shortcomings of the prior art. The patent discloses a dilator having a relatively small cutting edge which projects laterally of the dilator body. Consequently there is considerable tissue dilation and a minimum of cutting, thereby achieving a greater tamponade effect, that is, a stopping of bleeding by pressure against the involved blood vessels. The apparatus of my patent utilizes a highly flexible leader separably attachable to the dilator. The flexibility of the leader eliminates the potential hazard of undesirably piercing the tracheal lumen wall and damaging adjacent tissues and organs. However, the apparatus and method for inserting the leader and subsequently removing it, and the sequence of procedural steps for locating the trachea tube in breathing position proved to be unnecessarily complicated, and the means for positively establishing proper location of the initially placed elements of the apparatus in the tracheal lumen were not completely satisfactory.

SUMMARY OF THE INVENTION

According to the present invention a tracheostomy apparatus and method are provided which utilize coaxially arranged outer and inner needles for insertion into the tracheal lumen. The inner needle preferably extends distally of the outer needle in stepped fashion to facilitate such insertion. A syringe attached to the inner needle facilitates the insertion and gives an immediate indication of penetration of the tracheal lumen by the inner needle, the syringe plunger being readily movable outwardly upon such penetration.

The apparatus includes a dilator which coaxially slidably mounts a trachea tube. The dilator is characterized by a recessed cutting edge located above a tapered introducer portion so that only that tissue is cut which is stretched across the edge upon forcible insertion of the introducer portion into the tracheal lumen. The resulting tamponade effect eliminates most bleeding.

The distal end of the dilator introducer portion mounts a flexible leader which is easily bendable or flexible at its tip to prevent any piercing of the tracheal lumen wall.

Upon penetration of the trachea by the outer and inner needles, the inner needle is removable, and the outer needle is slotted to permit threading of the leader into the now vacant outer needle bore. This is followed by withdrawal of the outer needle to permit the dilator to be forced into the tracheal lumen along the path defined by the leader.

A trachea tube carried by the dilator is also carried into the tracheal lumen, being left in breathing position upon slidable withdrawal of the dilator.

In one embodiment of the invention, the exterior of the inserted trachea tube carries a deflated cuff to which an inflating tube is attached. The cuff is inflated through the syringe to thereby block entry into the trachea tube area of foreign matter from the head and upper throat.

Other objects and features of the invention will become apparent from consideration of the following description taken in connection with the accompanying drawings.

BRIEF DESCRIPTION OF THE DRAWINGS

FIG. 1 is an elevational view of the inner and outer needles of the present tracheostomy apparatus, a syringe being utilized to facilitate initial insertion of the needles into the tracheal lumen;

FIG. 2 is a view similar to FIG. 1 but illustrating the inclined advanced position into which the outer and inner needles are oriented subsequent penetration of the trachea by the inner needle;

FIG. 3 is a view similar to FIG. 2, but illustrating the outer needle subsequent withdrawal of the syringe and inner needle;

FIG. 4 is a view similar to FIG. 3, illustrating threading of the dilator leader into the outer needle slot;

FIG. 11 is a modified form of trachea tube mounting a collapsible cuff connected by a tube to a syringe for inflation;

FIG. 12 is an enlarged view taken along the line 12—12 of FIG. 11;

FIG. 13 is an enlarged view taken along the line 13—13 of FIG. 11;

FIG. 14 is an enlarged view taken along the line 14—14 of FIG. 11;

FIG. 15 is a side elevational view of the trachea tube in position within the trachea, and the dilator almost completely withdrawn; and FIG. 16 is a view similar to FIG. 15, illustrating the trachea tube in position subsequent withdrawal of the dilator and the trachea tube inner cannula.

DESCRIPTION OF THE PREFERRED EMBODIMENTS

Figure 5:
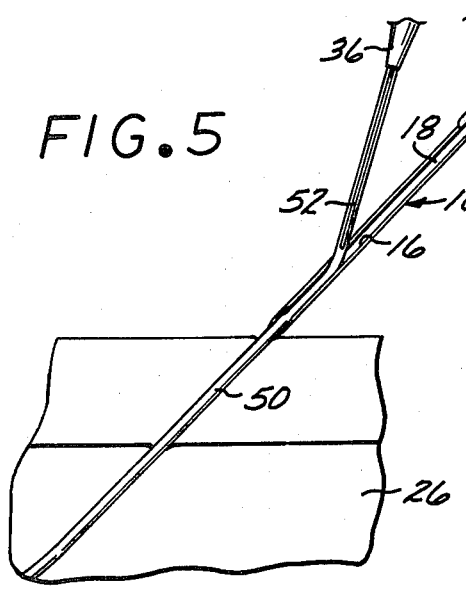
FIG. 5 is a view similar to FIG. 4, illustrating lateral separation of the leader from the outer needle during withdrawal of the outer needle.

As will be seen from the description which follows, the present tracheostomy apparatus and method are employed to perform a percutaneous tracheostomy, in contrast to a dissection tracheostomy which involves extensive surgical cutting of tissues and attendant skill. The present apparatus and method do not require the same level of skill to perform a tracheostomy, and consequently the method and apparatus are adapted for use in emergency situations by persons not having extensive surgical training. The nature of the apparatus is such that an essentially dilating action occurs in the formation of the opening for the trachea breathing tube, rather than a cutting action, resulting in a desirable tamponade effect. That is, the apparatus inserts the trachea tube in a manner such that the tube is pressed against the adjacent blood vessels and substantially eliminates bleeding.

The initial steps of the present method utilize a needle in association with a syringe. This enables immediate and positive signalling of the proper location of the needle within the tracheal lumen, which is critical to a successful tracheostomy. Another important feature is the utilization of a flexible leader to properly guide the trachea tube into the tracheal lumen through the initial opening formed by the needle. The flexibility of the leader permits it to bend and slide along the walls of the trachea, eliminating possible penetration and danger to the esophagus and large neck vessels. Indeed, it has been found that proper location of the leader within the tracheal lumen, and the attendant stimulating or tickling contact with the mucosal nerves, typically causes a desirable responsive patient coughing, which further verifies to the physician or attendant that the leader is properly located in the tracheal lumen.

Details of the general type of tracheostomy to which the present apparatus and method are directed are particularly set forth in my U.S. Pat. No. 3,511,243. In general, an initial incision is preferably made in the neck to facilitate insertion of a hollow needle, followed by insertion of a leader which is followed by a dilator designed to progressively enlarge or expand the needle opening occupied by the leader, followed by placement of a breathing or trachea tube. The tube provides a breathing passageway.

As will be apparent to those skilled in the medical arts, the various components of the present apparatus are configured and dimensioned to suit the size and condition of the patient, the dimensions being made smaller in the case of children, for example.

With respect to the particular details of the present tracheostomy apparatus and method, the figures of the drawings generally follow the sequence of steps characterizing the practice of the method of the present invention. Thus, in FIG. 1, the present apparatus comprises an elongated outer needle 10 having an enlarged upper body 12 to which are secured laterally extending wings or tabs 14. The distal end of the needle 10 is wedge-shaped to facilitate penetration of the trachea and associated tissue and cartilage. The needle 10 is also characterized by an elongated channel or slot 16 opening into a central bore 18 of the needle 10.

A hollow inner needle 20, similarly wedge-shaped at its distal end, is coaxially slidably received within the outer needle bore 18 and is characterized by an upper body 22 which is engageable upon the outer needle upper body 12 upon establishment of a predetermined degree of projection of the distal end of the inner needle 20 beyond the distal end of the outer needle 10, as best seen in FIG. 1.

The projection of the needle 20 beyond the needle 10 is desirable to provide a stepped increase in the cross-section of the inserted combination of needles 10 and 20 to facilitate insertion and penetration of the tissue and cartilage surrounding the tracheal lumen.

A usual and conventional syringe 24 is detachably coupled in fluid tight relation to the upper body 22 of the inner needle 20 whereby location of the distal end of the inner needle 20 within the tracheal lumen 26 is signalled to the physician or attendant through his ability to withdrawn the syringe plunger 28. That is, the plunger 28 can be withdrawn only if air from the trachea is able to enter the bore of the inner needle for entry into the hollow barrel of the syringe 24. In this regard, the desired projection of the distal end of the inner needle 20 beyond the distal end of the outer needle 10 eliminates the possibility that air entering the syringe barrel is being drawn from the bore 18 of the outer needle 10, which could possibly occur if the distal ends of both needles 10 and 20 were coterminous.

Once the inner needle 20 has entered the trachea, as illustrated in FIG. 1, it is angled at approximately a 45° angle in a direction down the throat, as illustrated in FIG. 2, and both needles 10 and 20 are next advanced approximately 6 to 8 millimeters.

The inner needle 20 and syringe 24 are slidably removed from the outer needle 10, as seen in FIG. 3, and next an elongated dilator 30 is employed to enlarge the opening for the trachea tube, as will be seen.

The dilator 30 includes an elongated handle portion, only a portion of which is illustrated at 32 in FIG. 4. The handle portion 32 is integral with a curve or arcuate intermediate portion 34 terminating in a conical introducer portion 36 which tapers from a larger diameter cross-section 38 to a smaller diameter cross-section 40. The larger diameter 38 of the introducer portion 36 is the same diameter as that of the intermediate portion 34. However, at its juncture with the intermediate portion 34, the handle portion 22 is larger in diameter than the intermediate portion 34 whereby a stop or shoulder is formed for a purpose which will be described.

A complementally curved metal trachea tube 42 is coaxially slidably fitted over the curved intermediate portion 34 of the dilator 30, as best seen in FIG. 4. The distal end of the trachea tube 42 includes a slot 45, and the opposing distal portions defining the slot 45 are deformed slightly inwardly so as to be able to closely grip the dilator intermediate portion 34 when the trachea tube 42 is mounted in the position illustrated in FIG. 4. Accordingly, separation between the tube 42 and dilator 30 cannot be accidental, but requires the deliberate application of an axially directed force.

The upper or proximal end of the trachea tube 42 includes a flat cap portion 44 which engages the shoulder defined at the juncture between the smaller dilator intermediate portion 34 and the larger handle portion 32, thereby locating the distal end of the trachea tube 42 just above a blade or cutting edge 46 mounted in a recess 48 formed in the intermediate portion 34 just above the larger diameter section 38 of the introducer portion 36. It is preferred that the cutting edge 46 not project outwardly of the exterior surfaces of the intermediate portion 34. This arrangement prevents cutting of any tissues except such tissues as are forcibly stretched across the intermediate portion 34 and into contact with the blade or edge 46.

The distal end of the introducer portion 36 mounts an elongated flexible leader 50. It is important that the leader 50 be sufficiently flexible that it will not under any circumstances penetrate the trachea wall or damage nearby blood vessels or the like.

Although the leader 50 may be made of any suitable material, it is conveniently made of a very thin tube of polyethylene material suitably affixed to the distal end of the dilator introducer portion 36. The leader 50 is preferably reinforced against significant bending at its proximal extremity by a wire 52 which is attached to the introducer portion 36 and which extends into the hollow interior of the leader 50, as best seen in FIGS. 4, 5 and 6.

By virtue of the construction just described, the leader 50 is easily threaded into the open upper end of the central bore 18 of the outer needle 10 for projection into the tracheal lumen, as seen in FIG. 4. Typically, the patient will cough or otherwise respond to the slight irritation of the tracheal mucosa on contact by the leader 50.

Use of the flexible leader 50 as an integral part of the dilator 30 greatly simplifies the tracheostomy procedure. Since it is flexible, the leader 50 tends to align itself with the trachea for later guiding of the dilator 30, as will be seen. In contrast, the relatively rigid leaders of the prior art devices require a surgeon's skill in accurately aiming the leader down the trachea axis. If not accurately aimed, the rigid leader or cutter of the prior art devices will cut through the tracheal wall.

Figure 6:
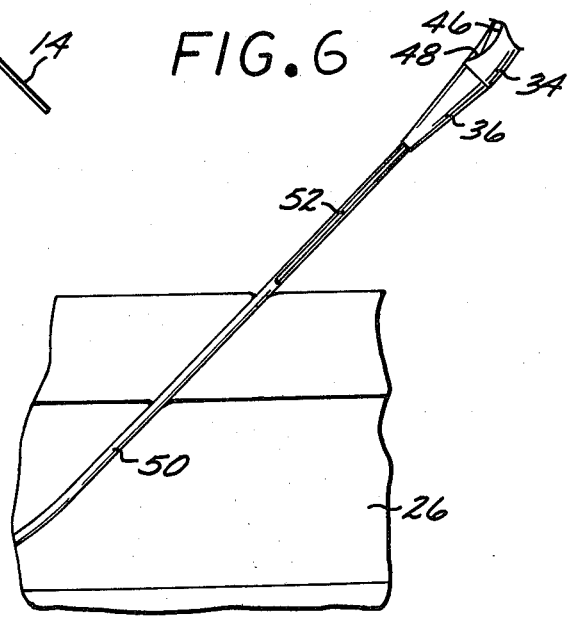
FIG. 6 is a view similar to FIG. 5, illustrating the dilator orientation prior to its penetration of the trachea.

Once the leader 50 is inserted to the extent illustrated in FIG. 4, the leader 50 is laterally separated from the outer needle 10 by pulling it out of the outer needle slot 16, as best seen in FIG. 5, while simultaneously withdrawing the needle 10.

Figure 7:
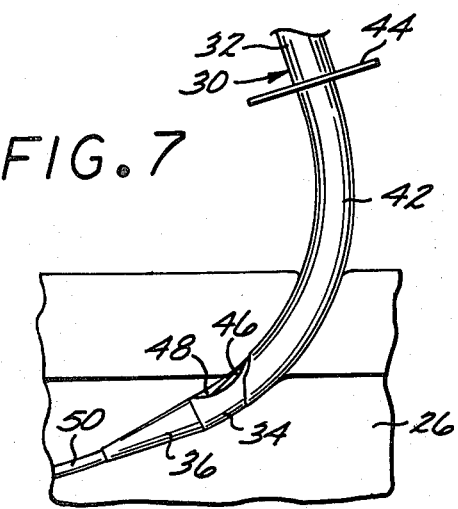
FIG. 7 illustrates initial penetration of the trachea by the dilator and trachea tube.

The axis of the dilator introducer portion 36 is next oriented at approximately a 45° angle, as seen in FIG. 6, and forced into the opening through which the leader 50 extends. The tissues are forced apart by the tapered introducer portion 36 and by the larger diameter trachea tube 42 which follows it. This dilating rather than cutting action minimizes bleeding and provides the desired tamponade effect. The only cutting of the tissues is that which is necessary to relieve the tension of tissues forcibly stretched across the intermediate portion 34 and into contact with the cutting edge 46. Cutting is only in proportion to the tension of the tissues stretched against the edge 46. Since the edge 46 is recessed it will not cut the endotracheal mucosa once it has entered the trachea, as seen in the successive showings of FIGS. 7 and 8.

Figure 8:
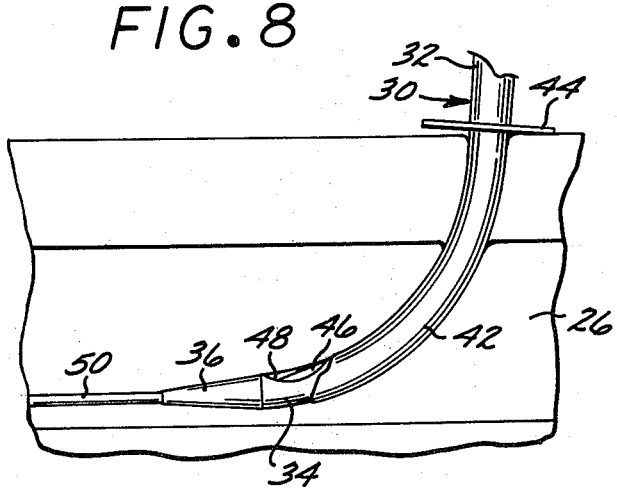
FIG. 8 is a view similar to FIG. 7, illustrating complete insertion of the trachea tube.
Figure 9:
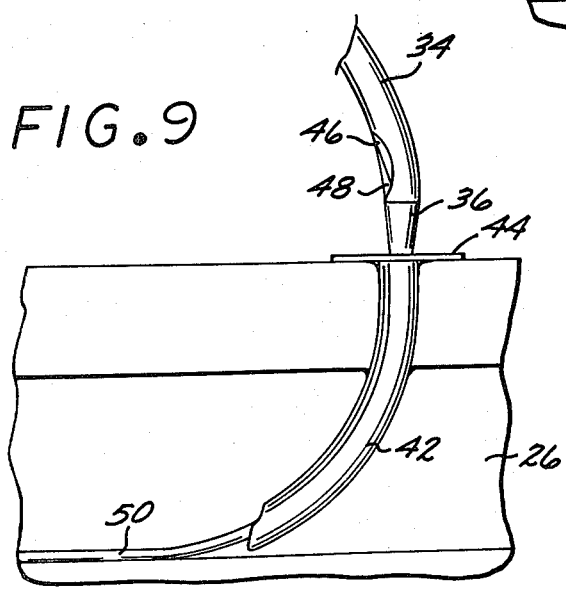
FIG. 9 is a view similar to FIG. 8, illustrating the dilator partially withdrawn.
Figure 10:
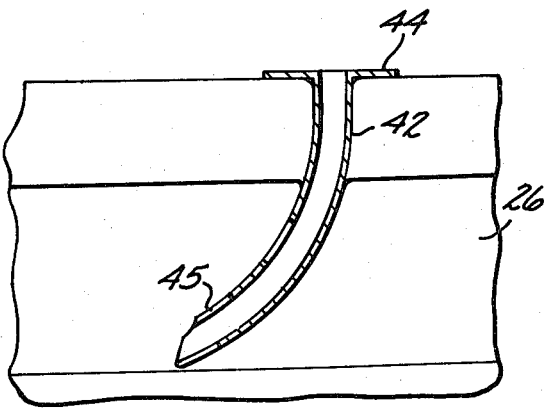
FIG. 10 is a cross-sectional view of the trachea tube in breathing position after removal of the dilator.

After the trachea tube cap portion 44 engages the throat, as seen in FIG. 8, the dilator 30 is withdrawn, as seen in FIG. 9, leaving the trachea tube 42 in position, as seen in FIG. 10.

If the patient cannot breathe normally through the trachea tube, and a respirator (not shown) is required, the tracheal lumen above the point of insertion of the trachea tube must be closed. For this purpose, a modified form of trachea tube 54 is employed, as best seen in FIGS. 11 through 16.

The tube 54 is substantially identical to the trachea tube 42 except that it is made slightly larger in diameter to provide a larger breathing passage. It is characterized by a stop plate or cap 44a having upwardly angled side margins which are slotted to receive a strap or thread or the like (not shown) for suturing or tying the tube 54 in place upon the patient.

In order for the larger diameter tube 54 to fit upon the dilator intermediate portion 34, a complementally curved or arcuate inner cannula 56 is telescopably slidably received within the central passage of the tube 54. The diameter of the cannula 56 is slightly greater than the inner diameter of the central passageway of the tube 54, and it is centrally slotted so that the cannula 56 is compressed slightly upon insertion within the tube 54. This insures against accidental withdrawal of the cannula 56 from the tube 54.

A cuff 58 made of thin polyethylene or other suitable material is adhesively attached to the exterior surface of the tube 54, as seen in FIGS. 11, 12 and 13.

The cuff 58 is collapsed closely upon the tube 54 prior to insertion of the tube 54 into the trachea, being arranged in loose and flexible folds, as seen in FIGS. 12 and 13. The cuff 58 is inflatable by means of a tube 60 terminating at one end within the cuff 58, as seen in FIG. 12, and opening into a bladder 62, as seen in FIG. 11.

The bladder 62 is pressurizable by depression of the plunger 28 of a conventional syringe 24 press-fitted within a receptacle 64 which forms an integral part of a valve case 66 having a plurality of apertures 68 in its base. The valve case 68 includes an integral shoulder or valve seat 70 normally engaged by a complemental shoulder of an axially movable valve 72 acting under the bias of a compression spring 74. Such engagement normally prevents passage of air from the interior of the valve case 66 to the exterior. However, upon insertion of the end of the syringe 24, as seen in FIG. 14, the valve 72 is unseated allowing air to pass from the syringe 24, through a slot 76 in the valve 72 to the base of the valve case 66, through the apertures 68, through the tube 60, and into the cuff 58.

The trachea tube 54 is inserted in the same manner described in connection with trachea tube 42, the deflated cuff 58 easily slidably entering the trachea, as seen in FIG. 15. The inner cannula 56 extends slightly beyond the trachea tube 54 to facilitate passage through the body tissues and is wedge shaped or cut on a bias for easier penetration. It is removed once the tube 54 is in breathing position.

The syringe 24 is operated to inflate the cuff 58, as seen in FIG. 16, thereby blocking the throat upwardly of the open distal end of the tube 54.

A respirator (not shown) can now be attached to the trachea tube 54 and operated in the usual fashion, as will be obvious to those skilled in the art.

Various modifications and changes may be made with regard to the foregoing detailed description without departing from the spirit of the invention.

I claim:
1. Tracheostomy apparatus comprising:
   a hollow outer needle having a central bore and a longitudinal slot opening into said bore;
   a hollow inner needle for attachment to a syringe and for coaxial slidable receipt within said bore for insertion of both said outer and inner needles into the tracheal lumen, said syringe being operable to withdraw air from said lumen thereby to confirm location of said needles in said lumen;

a trachea tube; and an elongated dilator coaxially slidably fitted through said trachea tube, and including a handle portion extending out of the proximal end of said trachea tube, and an introducer portion extending out of the distal end of said trachea tube and tapering distally from a larger diameter to a smaller diameter, said dilator further including an elongated, flexible leader non-separably carried by said introducer portion and adapted for insertion through said bore of said outer needle and into said tracheal lumen subsequent withdrawal of said inner needle whereby said outer needle is removable from said tracheal lumen by passage of said leader laterally out of said slot, the proximal end of said introducer portion including a recessed cutting edge for cutting tissue stretched across it upon forcible insertion of said introducer portion and said trachea tube into said lumen along the path defined by said leader.

2. Tracheostomy apparatus according to claim 1 wherein said inner needle extends distally of said outer needle to facilitate said insertion.

3. Tracheostomy apparatus according to claim 2 wherein the distal ends of said inner and outer needles are wedge shaped to facilitate said insertion.

4. Tracheostomy apparatus according to claim 1 wherein said trachea tube is metal, the distal end of said trachea tube includes a slot, and the confronting portions of said trachea tube defining said slot are deformed toward each other for clamping engagement upon said dilator to constrain said trachea tube against accidental axial movement relative to said dilator.

5. Tracheostomy apparatus according to claim 1 and including an inflatable cuff attached to said trachea tube; and inflating means coupled to said cuff for inflation thereof and consequent blockage of said lumen.

6. Tracheostomy apparatus according to claim 5 wherein said inflating means comprises a flexible tube in fluid communication with said cuff; and a syringe in fluid communication with said tube whereby operation of said syringe is adapted to inflate said cuff with the contents of said syringe.

7. Tracheostomy apparatus comprising:

a hollow outer needle having a central bore and a longitudinal slot opening into said bore:

a hollow inner needle for attachment to a syringe and for coaxial slidable receipt within said bore for insertion of both said outer and inner needles into the tracheal lumen, said syringe being operable to withdraw air from said lumen thereby to confirm location of said needles in said lumen:

a trachea tube;

a tubular inner cannula made of resilient material, axially slidably disposed within said trachea tube, and having an axial slot whereby the confronting portions of said inner cannula defining said slot are inwardly, resiliently deformable toward each other for biased engagement upon said trachea tube to constrain said inner cannula against accidental axial movement relative to said trachea tube; and an elongated dilator coaxially slidably fitted through said trachea tube, and including a handle portion extending out of the proximal end of said trachea tube, and an introducer portion extending out of the distal end of said trachea tube and tapering distally from a larger diameter to a smaller diameter, said dilator further including an elongated, flexible leader carried by said introducer portion and adapted for insertion through said bore of said outer needle and into said tracheal lumen subsequent withdrawal of said inner needle whereby said outer needle is removeable from said tracheal lumen by passage of said leader laterally out of said slot, the proximal end of said introducer portion including a recessed cutting edge for cutting tissue stretched across it upon forcible insertion of said introducer portion and said trachea tube into said lumen along the path defined by said leader.

8. Tracheostomy apparatus according to claim 5 wherein the distal ends of said trachea tube and inner cannula are wedge shaped to facilitate insertion thereof into said lumen.

9. Tracheostomy apparatus comprising:

a hollow outer needle having a central bore and a longitudinal slot opening into said bore;

a hollow inner needle for attachment to a syringe and for coaxial slidable receipt within said bore for insertion of both said outer and inner needles into the tracheal lumen, said syringe being operable to withdraw air from said lumen thereby to confirm location of said needles in said lumen;

a trachea tube; and an elongated dilator coaxially slidably fitted through said trachea tube, and including a handle portion extending out of the proximal end of said trachea tube, and an introducer portion extending out of the distal end of said trachea tube and tapering distally from a larger diameter to a smaller diameter, said dilator further including an elongated, flexible leader carried by said introducer portion and adapted for insertion through said bore of said outer needle and into said tracheal lumen subsequent withdrawal of said inner needle whereby said outer needle is removable from said tracheal lumen by passage of said leader laterally out of said slot, the proximal end of said introducer portion including a recessed cutting edge for cutting tissue stretched across it upon forcible insertion of said introducer portion and said trachea tube into said lumen along the path defined by said leader, said leader being made of tubular plastic material, and including a wire located within the proximal extremity of said leader and attached to said introducer portion, and operative to stiffen said proximal extremity adjacent said introducer portion to facilitate insertion of said leader through said bore of said outer needle.

10. An tracheostomy method comprising the steps of:

forming an entry to the tracheal lumen by insertion of the inner needle of coaxially arranged outer and inner needles;

withdrawing air from said lumen through said inner needle to confirm location of said inner needle in said lumen;

orienting said outer and inner needles down the patient's throat at an angle of approximately 45 degrees relative to the lumen axis and advancing said outer and inner needles into said lumen to insure location of said outer needle in said lumen;

withdrawing said inner needle and threading a flexible leader fixed to a dilator through the central bore of said outer needle until said leader engages, bends and slides along the tracheal mucosa;

laterally separating said leader from said outer needle through a longitudinal slot in said outer needle while withdrawing said outer needle;

mounting a trachea tube to said dilator and projecting said dilator and trachea tube into the trachea along the opening defined by said leader; and withdrawing said dilator and associated said leader from said lumen and said trachea tube.

11. A tracheostomy method according to claim 10 and including the steps of mounting an inflatable cuff to said trachea tube prior to projecting said trachea tube into said lumen; and inflating said cuff after projecting said trachea tube into said lumen to block said lumen.

* * * * *

UNITED STATES PATENT AND TRADEMARK OFFICE
CERTIFICATE OF CORRECTION

PATENT NO. : 4,364,391

DATED : December 21, 1982

INVENTOR(S) : Frederic J. Toye

It is certified that error appears in the above-identified patent and that said Letters Patent is hereby corrected as shown below:

Column 1, line 23, delete "if" and insert --is--; and

Column 8, line 14, delete "5" and insert --7--.

Signed and Sealed this

First Day of March 1983

[SEAL]

Attest:

GERALD J. MOSSINGHOFF

Attesting Officer    Commissioner of Patents and Trademarks